United States Patent [19]
Efrat

[11] Patent Number: 6,114,599
[45] Date of Patent: Sep. 5, 2000

[54] RECOMBINANT β-CELL AND USES THEREOF

[75] Inventor: Shimon Efrat, Bronx, N.Y.

[73] Assignee: Albert Einstein College of Medicine of Yeshiva University, Bronx, N.Y.

[21] Appl. No.: 09/044,297

[22] Filed: Mar. 19, 1998

Related U.S. Application Data

[62] Division of application No. 08/418,416, Apr. 7, 1995, abandoned.

[51] Int. Cl.[7] .................. A01K 67/027; C21N 15/00; C21N 5/00; C21N 5/06; C21N 15/63
[52] U.S. Cl. .................. 800/21; 800/18; 800/22; 800/25; 424/93.21; 435/325; 435/354; 435/366; 435/455
[58] Field of Search .................. 435/325, 354, 435/455, 366; 800/13, 14, 18, 21, 22, 25

[56] References Cited

U.S. PATENT DOCUMENTS

| | | | |
|---|---|---|---|
| 5,776,747 | 7/1998 | Schinstine et al. | 435/177 |
| 5,795,790 | 8/1998 | Schinstine et al. | 435/382 |
| 5,935,849 | 8/1999 | Schinstine et al. | 435/325 |

OTHER PUBLICATIONS

D'Ambra et al. Regulation of insuling secretion from beta–ell lines derived from transgenic mice insulinomas resembles that of normal beta–cells. Endocrinology 126(6): 2815–2822, 1990.

Gossen et al. Tight control of gene expression in mammalian cells by tetracycline–responsive promoters. Proc. Natl. Acad. Sci. USA 89: 5547–5551, Jun. 1992.

Hammer et al. Spontaneous inflammatory disease in transgenic rats expressing HLA–B27 and human b2m: An animal model of HLA–B27–associated human disorders. Cell 63: 1099–1112. Nov. 1990.

Mullins et al. Expression of the DBA/2J Ren–2 gene in the adrenal gland of transgenic mice. EMBO J. 8(13): 4065–4072, 1989.

Mullins et al. Fulminant hypertension intransgenic rats harbouring the mouse Ren–2 gene. Nature 344: 541–544, Apr. 1990.

Taurog et al. HLA–B27 in inbred and non–inbred transgenic mice. J. of Immunol. 141(11): 4020–4023, Dec. 1988.

Wall, RJ Transgenic livestock: Progress and prospects for the future. Theriogenology 45: 57–68, 1996.

*Primary Examiner*—Jasemine Chambers
*Assistant Examiner*—Anne-Marie Baker
*Attorney, Agent, or Firm*—Amster, Rothstein & Ebenstein

[57] ABSTRACT

The present invention provides a recombinant, glucose-regulated insulin producing beta cell whose proliferation is controlled by tetracycline or a derivative thereof. The present invention also provides a method for treating a subject with diabetes using the recombinant beta cell of the present invention.

5 Claims, 6 Drawing Sheets

RECOMBINANT β-CELL AND USES THEREOF

This application is a divisional application of U.S. patent application Ser. No.: 08/418,416, filed Apr. 7, 1995 now abandoned.

BACKGROUND OF THE INVENTION

Diabetes mellitus is a chronic disorder of carbohydrate metabolism characterized by insufficient production of insulin by the pancreatic beta cells. Diabetes effects approximately 10 million people in the United States, with more than 250,000 new cases diagnosed each year. There are two common types of diabetes mellitus: insulin-dependent (Type-I diabetes) and non-insulin-dependent (Type-II diabetes). Insulin-dependent diabetes is generally characterized by an absolute deficiency of insulin production, whereas non-insulin-dependent diabetes is characterized by a relatively insufficient production of insulin.

In normal individuals, the rate of insulin secretion by beta cells is regulated by the level of glucose in the blood. When the blood glucose level rises, the islet cells are stimulated to release increased amounts of insulin into the blood, accelerating glucose transport into the cells and glucose conversion into glycogen. As the blood glucose level falls, insulin release from the islets is decreased. In the diabetic subject, insulin production is abnormally low or insufficient, resulting in abnormally high blood glucose levels, a condition known as hyperglycemia.

In addition to diet and exercise programs, the constant and life long monitoring of blood glucose levels in conjunction with injections of insulin is central to the current methods for the treatment of the insulin-dependent diabetic subject. Many diabetic subjects, however, have difficulty in controlling their blood glucose levels using the current treatment methods, thus constantly exposing themselves to the adverse effects of hypoglycemia (abnormally low blood glucose levels) and hyperglycemia.

The inability to precisely control the level of blood glucose also poses long term complications such as degenerative vascular changes (e.g. atherosclerosis and microangiopathy), neuropathy (e.g. peripheral nerve degeneration, autonomic nervous system, and cranial nerve lesions), ocular disturbances (e.g. blurred vision, cataracts, and diabetic retinopathy), kidney diseases (e.g. recurrent pyelonephritis and nephropathy), and infections. Accordingly, there exists a need for an alternative method for controlling blood glucose levels in the diabetic patient. The transplantation of beta cells has been proposed as an alternative therapy in the treatment of diabetes. However, large scale transplantation of human beta cells is not feasible because of the limited availability of donors; similarly, the cost and effort, in terms of labor, associated with obtaining sufficient amounts of animal islets for transplantation also limits their use. These and other disadvantages associated with transplanting human and animal islets, makes the development of islet-derived cell lines the method of choice in obtaining sufficient quantities of cells for transplantation. In particular, a number of beta cell lines have been generated from insulinomas and hyperplastic islets arising in mice expressing a transgene encoding the SV40 T antigen (Tag) oncogene under the control of the insulin promoter (RIP-Tag)(1-6). Several of these cell lines displayed insulin secretion characteristics similar to those observed in intact adult islets, in particular the response to glucose concentrations in the physiological range (5–15 mmol/l).

However, a common problem encountered with all of these cell lines is their phenotypic instability. After propagation in tissue culture, these cells become responsive to subphysiological concentrations of glucose and/or manifest diminished insulin output (4, 6–9). A similar instability has been observed with beta cell lines derived by other methods (10–12).

The present invention overcomes the problems associated with the previous beta cell lines by providing a beta cell line which not only maintains blood glucose levels in the normal range, but also may be controlled to prevent unregulated proliferation.

SUMMARY OF THE INVENTION

The present invention provides a recombinant, glucose-regulated insulin producing beta cell whose proliferation is controlled by tetracycline or a derivative thereof.

The present invention also provides a microcapsule comprising an amount of the recombinant beta cell above sufficient to maintain physiologically acceptable levels of glucose in a subject implanted with the microcapsule.

The present invention also provides a method for treating a subject with diabetes which comprises (a) implanting in the subject recombinant, beta cells whose proliferation is controlled by tetracycline or a derivative thereof, in an amount effective to establish and maintain physiologically acceptable levels of glucose in the blood of the subject; and (b) inhibiting proliferation of the implanted recombinant beta cells by administering to the subject an amount of tetracycline or a derivative thereof, effective to inhibit proliferation of the implanted recombinant beta cells.

The present invention also provides a method for producing a recombinant, glucose-regulated insulin producing beta cell whose proliferation is controlled by tetracycline or a derivative thereof, comprising the steps of: (a) introducing to a first, non-human animal a first plasmid comprising a DNA encoding a tetR-VP16 fusion protein, and an insulin promoter which controls expression of the fusion protein, such that a first, genetically-controlled, non-human animal is obtained; (b) introducing to a second, non-human animal a second plasmid comprising a DNA encoding the SV40 T antigen, and a tetracycline (Tc) operator minimal promoter, such that a second genetically-modified, non-human animal is obtained; (c) crossing the first genetically-modified, non-human animal, or offspring thereof, with the second, genetically-modified, non-human animal, or offspring thereof, to obtain progeny; (d) screening the progeny for double transgenic, non-human animals which bear beta cell tumors, the proliferation of which can be controlled by tetracycline or a derivative thereof; and (e) then isolating the beta cells.

The present invention also provides a method for producing recombinant, glucose-regulated insulin producing beta cells whose proliferation is controlled by tetracycline or a derivative thereof, comprising the steps of: (a) introducing into a beta cell, a first gene comprising a DNA encoding a TetR-VP16 fusion protein, and an insulin promoter which controls expression of the fusion protein, and a second gene comprising a DNA encoding SV40 T antigen, and a tetracycline operator minimal promoter, such that stable integration of both genes is acheived; and (b) screening for cells whose proliferation is controlled by tetracycline or a derivative thereof.

The present invention further provides a method for producing recombinant cells whose proliferation is controlled by tetracycline or a derivative thereof, comprising the steps of: (a) introducing to a first, non-human animal a first plasmid comprising a DNA encoding a tetR-VP16 fusion protein, and a promoter specific to said cell which controls expression of said fusion protein, such that a first, genetically-modified, non-human animal is obtained; (b) introducing to a second, non-human animal a second plasmid comprising a DNA encoding SV40 T antigen, and a tetracycline operator minimal promoter, such that a second, genetically-modified, non-human animal is obtained; (c) crossing said first, genetically-modified, non-human animal, or offspring thereof, with said second, genetically-modified, non-human animal, or offspring thereof, to obtain progeny thereof; (d) screening said progeny for double-transgenic, non-human animals which bear tumors, the proliferation of which is controlled by tetracycline, or a derivative thereof; and (e) isolating said cells.

Lastly, the present invention provides a method for producing recombinant cells whose proliferation is controlled by tetracycline or a derivative thereof, comprising the steps of: (a) introducing into a cell, a first gene comprising a DNA encoding a TetR-VP16 fusion protein, and a promoter specific to said cell which controls expression of said fusion protein, and a second gene comprising a DNA encoding SV40 T antigen, and a tetracycline operator minimal promoter, such that stable integration of both genes is achieved; and (b) screening for cells whose proliferation is controlled by tetracycline or a derivative thereof.

BRIEF DESCRIPTION OF THE FIGURES

FIG. 1 is comprised of FIGS. 1A and 1B, and represents gene constructs used in the conditional transformation strategy.

DETAILED DESCRIPTION OF THE INVENTION

Figures 1A, 1B:
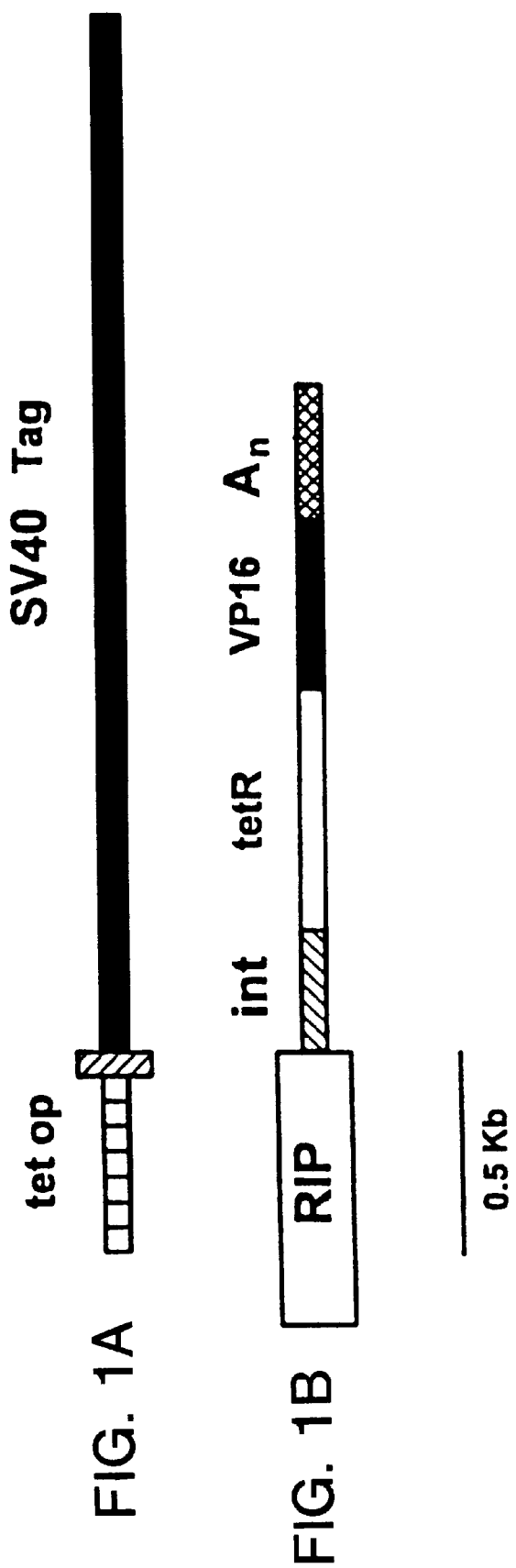
FIG. 1A depicts the tet-Tag construct. The SV40 Tag gene was placed under the control of a tandem array of Tc operator sequences and a minimal promoter (hatched box).
FIG. 1B depicts the RIP-tTA construct. A fusion gene encoding the tetR and the activating domain of the HSV VP16 protein was placed under the control of the RIP promoter, downstream of an intron element (int) and upstream of a polyadenylation signal ($A_n$).

The present invention provides a recombinant, human or animal, glucose-regulated insulin producing beta cell whose proliferation can be controlled by incubating the cell with tetracycline or one of its derivatives. In the preferred embodiment of the present invention, the recombinant beta cell is contained within the cell line designated βTC-tet, which was deposited under the terms of the Budapest Treaty on Mar. 31, 1995 with the American Type Culture Collection (ATCC), Rockville, Md., and assigned ATCC Accession Number CRL-11869. Vitality of the cell line was confirmed on Apr. 6, 1995. The present invention also provides the beta cell line deposited with the ATCC under Accession Number CRL-11869.

The recombinant beta cell of the present invention may be produced by crossing two lineages of non-human transgenic animals such as cows, pigs, mice, and are preferably mice. The beta cells of one lineage contain a fusion protein consisting of the tetR and the activating domain of the HSV VP16 protein under the control of an insulin promoter. The combination of tetR and the HSV VP16 sequence converts the tetR into a transcription activator. The other lineage of transgenic mice contains the Tag gene under the control of a tandem array of Tc operator sequences, and a minimal promoter. The minimal promoter alone is incapable of directing expression of the Tag gene. However, in the presence of the tetR-VP16 transcription activator, denoted the tetracycline-controlled transactivator (tTA), Tag gene expression is activated. In the double transgenic mice, Tag is expressed and this expression results in beta cell tumors. Beta cell tumors whose proliferation is inhibited by tetracycline or one of its derivatives, are then selected to obtain the beta cell of the present invention.

The recombinant beta cell of the present invention may also be produced by the introduction into beta cells in tissue culture of a first gene encoding a fusion protein consisting of the tetR and the activating domain of the HSV VP16 protein under the control of an insulin promoter together with a second gene encoding the SV40 T antigen under the control of a tandem array of Tc operator sequences, and a minimal promoter. The beta cells can be, but are not limited to, beta cells of cow, pig, mouse or human origin, and are preferably of human origin. The genes can be introduced by stable transfection of the beta cells by methods well known to those skilled in the art such as calcium phosphate precipitation, cationic liposome fusion or electroporation. Alternatively, the genes can be introduced into the beta cells using viral vectors such as herpes virus-, adenovirus- or retrovirus-based vectors by techniques well known to those skilled in the art. Beta cells whose proliferation is inhibited by tetracycline or one of its derivatives are then selected to obtain the beta cell of the present invention.

The recombinant beta cell, by virtue of its retention of normal beta cell characteristics with regard to insulin secretion and blood glucose regulation, offers an alternative to insulin administration in the treatment of diabetes in both animals and humans. Accordingly, the present invention also provides a method for treating a diabetic subject. The method comprises implanting recombinant beta cells in the body of the diabetic subject in an amount effective to establish and maintain physiologically acceptable levels of blood glucose; and then inhibiting the proliferation of the recombinant beta cells by administering tetracycline or one of its derivatives in an amount sufficient to inhibit the proliferation of the recombinant beta cells. The beta cells may be implanted in any feasible location within the body where they come in contact with the blood stream of the recipient. Suitable locations include but are not limited to the peritoneal cavity and the pancreas. Other locations would be apparent to one skilled in the art. The beta cells may be implanted by methods known to those skilled in the art such as by surgical means, injection and the like. The effective amount of beta cells is preferably about 100 to about 300 million cells. The effective amount of beta cells, however, will depend upon the method of implantation, the pharmacokinetic characteristics of the subject treated, and/or the presence of other diseases or conditions. Such amounts are readily determined by one skilled in the art.

Rejection of the implanted beta cells may be controlled by administration of immunosuppressant drugs such as cyclosporine or azathioprine and the like. Alternatively, the beta cells may be microencapsulated prior to implantation. The term "microencapsulation" as used herein means any method which may be used to protect foreign cells introduced into the body of a recipient from destruction by the recipient's immune system. Microencapsulation methods include but are not limited to the methods described in U.S. Pat. Nos. 5,389,535, 5,334,640, and tissue inplant systems described in U.S. Pat. Nos. 5,314,471, and 5,344,454, which are hereby incorporated by reference. Other means for microencapsulating the beta cells or alternative tissue implant systems would be apparent to one skilled in the art.

The present invention also provides a microcapsule comprising an amount of the above beta cell which is sufficient to maintain physiologically acceptable levels of glucose in a subject implanted with the microcapsule. Preferably, beta cells are obtained from the cell line deposited with the ATCC under Accession Number CRL-11869. As above, the amount of beta cells may be about 100 to about 300 million cells. Again, the actual amount will depend upon the method of implantation, the pharmacokinetic characteristics of the subject treated, and/or the presence of other diseases or conditions. Such amounts are readily determined by one skilled in the art. The term "microcapsule" as used herein means any vehicle, polymer composition or like means used in a microencapsulation process for implantation into the body of a subject.

Tetracycline is commercially available from Sigma Chemical Co., St. Louis, Mo. Tetracycline derivatives include but are not limited to anhydrotetracycline, 7-chloro-tetracycline, 4-Epi-7-chloro-tetracycline, oxy-tetracycline, doxycycline, 6-deoxy-6-demethyl-tetracycline, and 7-azido-6-deoxy-6-demethyl-tetracycline. These derivatives and others are commercially available. Anhydrotetracycline is preferred because it binds tetR more efficiently than tetracycline and has a lower antibiotic activity, thereby enabling long term administration. Tetracycline and its derivatives can be administered orally, by intravenous or intramuscular injection. Other modes of administration would be apparent to one skilled in the art. The amount of tetracycline is an amount effective to inhibit the proliferation of beta cells. The actual dosage will depend upon the route of administration and the individual pharmacokinetic parameters of the subject treated. The actual dosage is readily determined by one skilled in the art.

The present invention also provides a general method for producing recombinant cell lines from a variety of cell types in addition to beta cells. Such cell lines may be produced by either of the methods previously described for generating recombinant beta cells. In producing such cells, however, the insulin promoter used to control the expression of the TetR-VP16 fusion protein in the beta cell, is replaced by a promoter specific to the cell type of interest. Such cell-specific promoters are well known to those skilled in the art. For example, in producing recombinant liver cells of the present invention, a liver-specific promoter such as the albumin promoter could be utilized.

The present invention is described in the following Experimental Details Section which is set forth to aid in the understanding of the invention, and should not be construed to limit in any way the invention as defined in the claims which follow thereafter.

Experimental Details Section

A. Materials and Methods

Plasmid constructs. Plasmids pUHD 10-3 and pUHD 15-1 were obtained from H. Bujard, Zentrum für Molekulare Biologie der Universität Heidelberg, Im Neuenheimer Feld 282, W-6900 Heidelberg, Germany. To construct the tet-Tag plasmid, the Xho I–Xba I fragment from pUHD 10-3 (13), containing a tandem array of 7 copies of the Tc operator sequence and a CMV minimal promoter, was placed in front of the T antigen gene in pRIP-Tag (14) by deleting the Aat II-Xba I fragment containing the RIP from pRIP-Tag and converting the Aat II and Xho I sites into blunt ends.

To generate pRIP-tTA, the EcoR I-BamH I tTa fragment from pUHD 15-1 (13) was made blunt-ended with Klenow and ligated into the Sma I site of pMLSIS.CAT (15), after removal of the Pst I—Sma I CAT fragment. This placed the tTA gene downstream of a hybrid intron element and upstream of the SV 40 late polyadenylation site. The combined 1630-bp fragment was inserted between the Xba I and Sal I sites of pRIP-Tag downstream of the rat insulin II promoter.

Transgenic mice. Linearized plasmid DNA was microinjected into 1-cell C3HeB/FeJ mouse embryos. Transgenic mice were generated and bred according to established procedures (16).

Cell culture. Tumors were excised from the pancreas, and β-cell line, denoted βTC-tet, was established and propagated as described (2). All media supplies were from GIBCO. Cells were grown in DMEM containing 25 mM glucose and supplemented with 15% horse serum, 2.5% fetal bovine serum, 100 U/ml penicillin and 100 µg/ml streptomycin. Tetracycline (United States Biochemical Corporation) and anhydrotetracycline (ATc) (Lederle) were included at the indicated concentrations.

Cell implantation. Cells were trypsinized, washed in PBS, and resuspended in PBS at $5 \times 10^6$ cells/ml. Recipient C3H mice were injected intraperitoneally (I.P.) with $10^6$ cells each and maintained on regular drinking water or on water containing 1 mg/ml Tc and 2.5% sucrose. Each group included 4–5 mice. They were monitored weekly for blood glucose using Glucometer strips. To generate diabetic mice, 12 C3H male mice were injected I.P. with one dose of 200 mg streptozotocin (Sigma) per Kg of body weight, followed 7 days later by 3 doses of 50 mg/Kg on 3 consecutive days, which caused hyperglycemia within 6–9 additional days. Eight mice were then injected I.P. with $2 \times 10^6$ βTC-tet cells, while 4 mice were kept as diabetic controls. Mice were monitored weekly for blood glucose levels. When euglycemia was obtained in the cell-implanted group, 4 of the mice in this group were implanted subcutaneously with a slow-release Tc pellet (Innovative Research of America) designed to release 3.3 mg per day, and were further followed by weekly blood glucose checks. Glucose levels below 40 mg/dl were determined using a Beckman glucose analyzer.

Immunohistochemistry. Cells were plated in 16-well slides (Nunc) for the indicated period in the absence or presence of Tc or ATc. For BrdU incorporation assay, cells were pulsed for 60 min with 10 µM BrdU (Sigma) and stained with an anti-BrdU monoclonal antibody (Becton-Dickinson) according to manufacturer's recommendations. The bound antibody was visualized with biotinylated anti-mouse IgG and horseradish peroxidase-conjugated avidin (Vector, ABC kit), and a diaminobenzidine (DAB) substrate. Cells in separate wells were stained with a rabbit-anti-Tag serum (17). The bound antibody was visualized with a horseradish peroxidase-conjugated goat-anti-rabbit antibody and DAB. Mice with βTC-tet tumors were injected I.P. with 100 µg BrdU/g body weight. One hour later they were sacrificed, and the tumors were removed, fixed with 4% buffered formaldehyde, processed for paraffin embedding, and sectioned. Tumor sections were stained with anti-Tag and anti-BrdU antibodies as described above.

Thymidine incorporation assay. $2 \times 10^4$ cells were seeded into 96-well plates. Following the indicated incubation, they were pulsed with 1 µCi [methyl-$^3$H]thymidine (Amersham, 78 Ci/mmol) for 6 h. The cells were then lysed in water using a cell harvester, and the DNA was retained on a glass fiber filter (Whittaker). The filters were dried, and the radioactivity incorporated into DNA was quantitated with a scintillation counter. Each condition was assayed in quadruplicates.

B. Results

The tTa gene was placed under control of RIP (FIG. 1), and the construct was used to generate transgenic mice, in which tTA would be constitutively expressed specifically in β cells. In a separate lineage of transgenic mice, the Tag gene was introduced under the control of a minimal promoter and a tandem array of Tc operator sequences (FIG. 1). This promoter does not allow expression of the gene by itself. Therefore, as expected, these transgenic mice did not develop tumors. The two lines of mice were crossed to generate double-transgenic mice. In these mice the tetR part of the tTA protein is expected to bind to the target Tc operator sequences in β cells and allow the VP16 part of the molecule to activate transcription of the Tag gene. This resulted in the development of multiple β-cell tumors by 5–6 months of age. No tumors were detected in other organs, demonstrating the need for the tTA-induced expression of Tag for the β-cell specific tumor development.

Figure 2A:
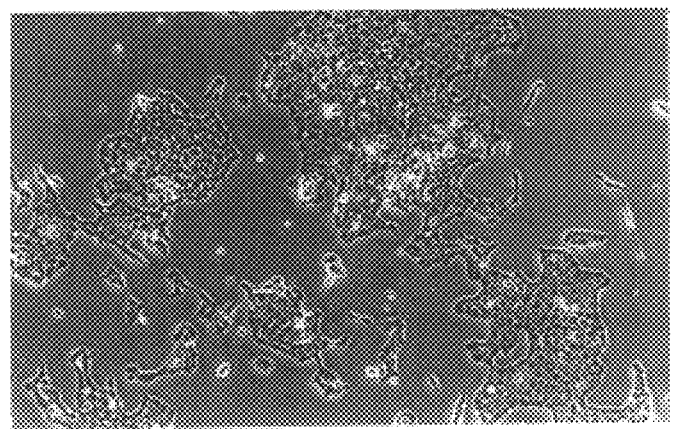
FIG. 2 is comprised of FIGS. 2A, 2B, 2C, 2D, 2E, and 2F, and represents the effect of Tc on βTC-tet cell growth and Tag expression. Equal numbers of βTC-tet cells were seeded into two series of wells. They were grown for 3 weeks in the absence (FIG. 2A) or presence (FIG. 2B) of 1 μg/ml Tc and photographed in a phase contrast microscope. Similar cells were incubated in 16-well slides for 7 days in the absence (FIGS. 2C and 2E) or presence (FIGS. 2D and 2F) of 1 μg/ml Tc. Cells were pulsed for 1 hour with BrdU (FIGS. 2C and 2D), and stained with an anti-BrdU monoclonal antibody. Cells in separate wells were stained with a Tag antiserum (FIGS. 2E and 2F). The bound antibodies were visualized with horseradish peroxidase-conjugated second antibodies. The cells shown are representative of 3 independent experiments. Magnification is ×200.
Figure 2B:
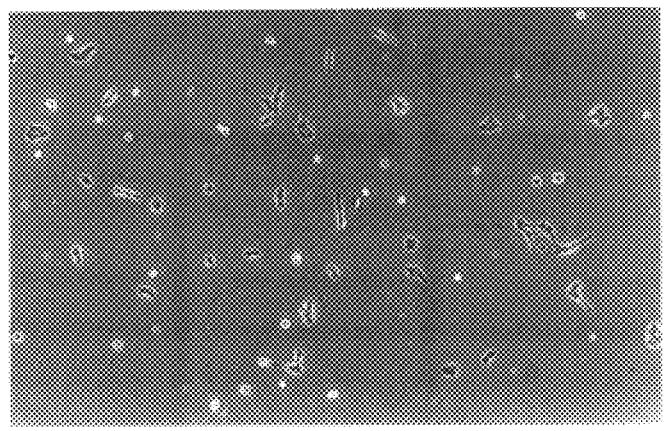
Figure 2C:
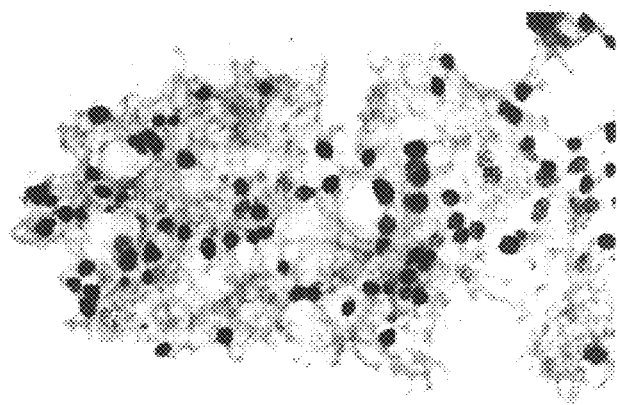
Figure 2D:
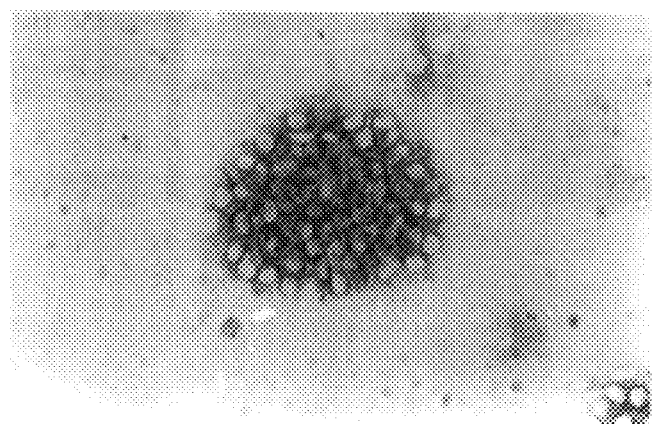
Figure 2E:
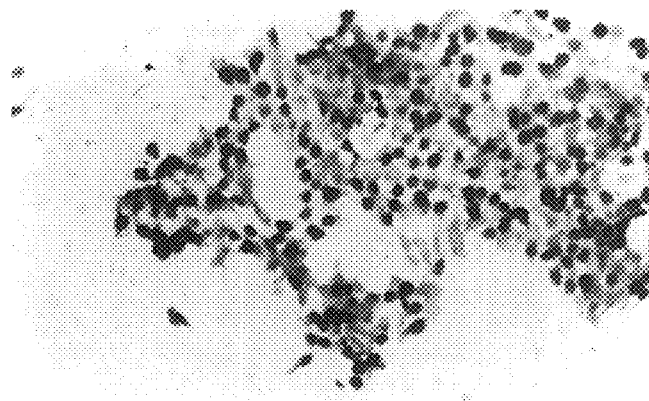
Figure 2F:
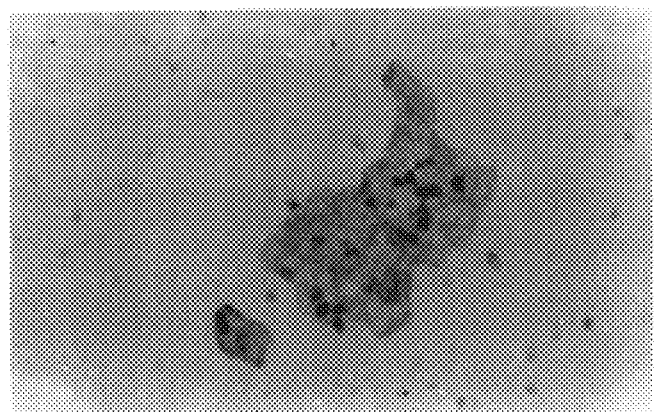

Cells from the tumors were cultured to derive a stable cell line, denoted βTC-tet. When incubated in the presence of 1 µg/ml Tc the cells undergo growth arrest, as demonstrated by the difference in cell number and size of the colonies between FIGS. 2A and 2B. This effect is reversible. Removal of Tc after a 3-week incubation resulted in resumed cell replication (not shown). The effect of Tc on DNA replication in the βTC-tet cells was analyzed by visualizing BrdU incorporation with an anti-BrdU monoclonal antibody. In the absence of Tc many replicating cells incorporated BrdU during a 1 hour pulse (FIG. 2C). Following a 3-day incubation in 1 µg/ml Tc, only a small number of cells incorporated BrdU (data not shown). After a 7-day incubation, no cells were observed to incorporate BrdU (FIG. 2D). The effect of Tc on Tag expression was analyzed by immunohistochemistry with a Tag antiserum. Following a 7-day incubation in 1 µg/ml Tc, Tag immunostaining disappeared from most of the cells (FIG. 2F). However, a small number of cells maintained detectable Tag staining.

Figure 3:
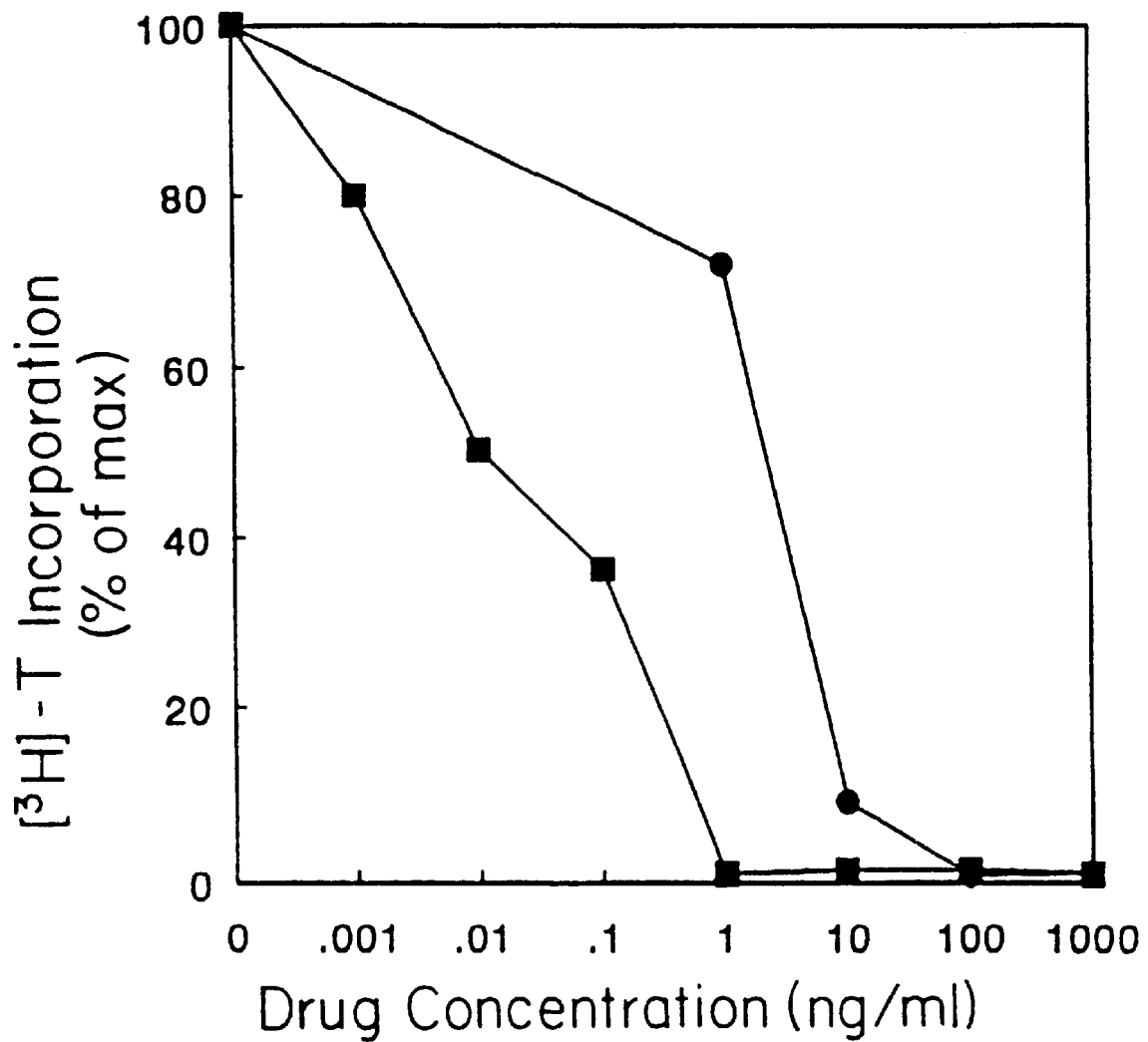
FIG. 3 represents the growth arrest of βTC-tet cells following incubation with Tc and anhydrotetracycline (ATc). $2 \times 10^4$ cells in quadruplicate wells were incubated for 7 days in the presence of the indicated concentration of Tc (circles) or ATc (squares). They were then pulsed with [$^3$H]thymidine for 6 h, followed by quantitation of the radioactivity incorporated into DNA. Values represent percent of counts in the absence of drugs, averaging $4 \times 10^4$ cpm per well.

The effect of various concentrations of Tc on cell growth was analyzed by $^3$H-thymidine incorporation into replicating DNA (FIG. 3). A complete shutoff of replication was achieved in the presence of 100 ng/ml of Tc. The binding of the Tc derivative ATc to TetR has been shown to be 35 times stronger than that of Tc to TetR (18). As shown in FIG. 3, incubation of βTC-tet cells in the presence of ATc resulted in complete growth arrest at 1 ng/ml.

Cells from another β-cell line, βTC3 (2), which was derived from mice expressing a RIP-Tag gene that is not responsive to the Tc regulation, were used as controls in these experiments. Incubation of βTC3 cells in the presence of 1 µg/ml of either Tc or ATc did not effect their growth rate, BrdU and $^3$H-thymidine incorporation, and Tag staining (not shown).

Figure 4A:
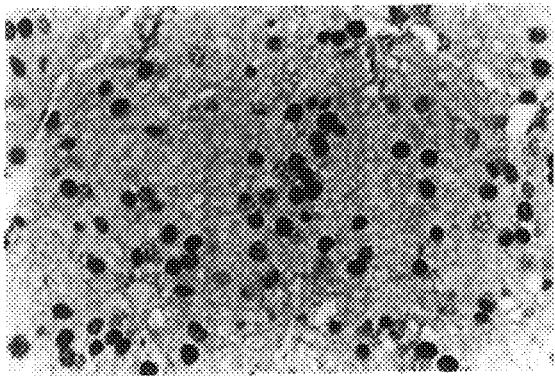
FIG. 4 is comprised of FIGS. 4A, 4B, 4C, and 4D, and represents the effect of Tc on Tag expression and βTC-tet cell proliferation in vivo. Mice with βTC-tet tumors received regular drinking water (FIGS. 4A and 4C) or water containing Tc (FIGS. 4B and 4D) for 7 days. They were then pulsed with BrdU (FIGS. 4A and 4B) and Tag (FIGS. 4C and 4D) antisera. The bound antibodies were visualized with horseradish peroxidase-conjugated second antibodies. Magnification is ×230.
Figure 4B:
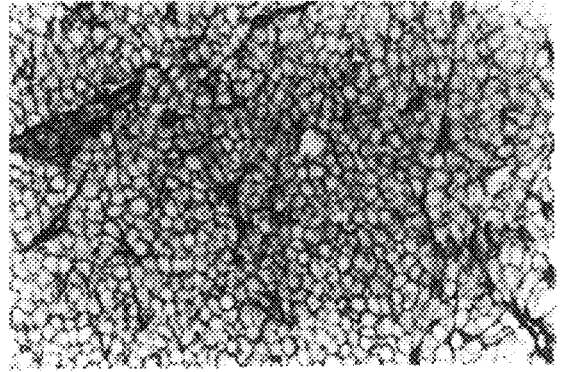
Figure 4C:
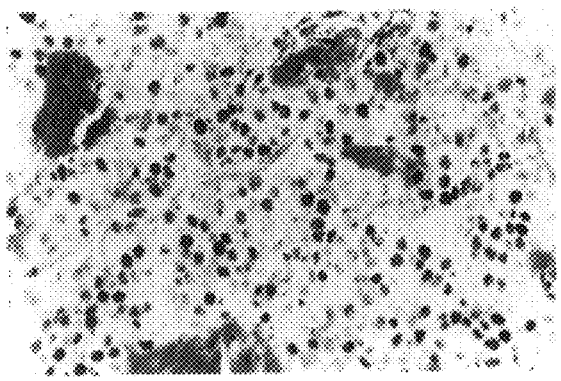
Figure 4D:
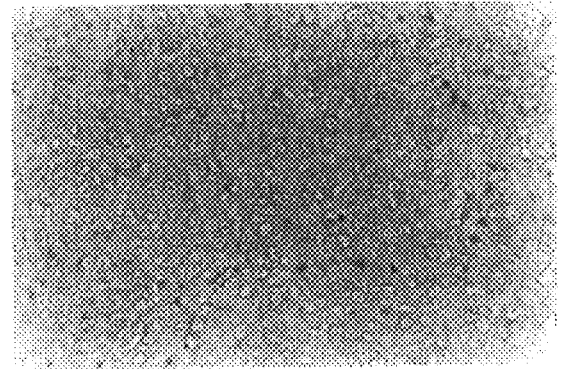

To test the ability of Tc to regulate cell growth in vivo, syngeneic C3H mice were injected with $10^6$ βTC-tet cells I.P. βTC cell lines are tumorigenic and form benign tumors at the site of injection (2). Tumor development leads to hypoglycemia and can be detected by monitoring blood glucose levels. Mice in one group were maintained on drinking water containing Tc. None of them developed tumors within 14 weeks, as judged by blood glucose measurements and a careful autopsy. No abnormalities were observed as a result of the prolonged Tc treatment. Mice maintained in the absence of Tc developed hypoglycemia and tumors within 8–13 weeks. When hypoglycemia was detected, one sub-group continued to drink regular water. The mice were then pulsed with BrdU, sacrificed, and the tumors were removed and processed for immunohistochemical analyses. Tumors from mice that were not treated with Tc contained numerous cells that stained for BrdU and Tag (FIGS. 4A and 4C). In contrast, tumors from mice treated for 7 days with Tc showed no BrdU and Tag staining (FIGS. 4B and 4D). These results demonstrate that Tc effectively inhibits Tag expression and β-cell proliferation in vivo.

Figure 5:
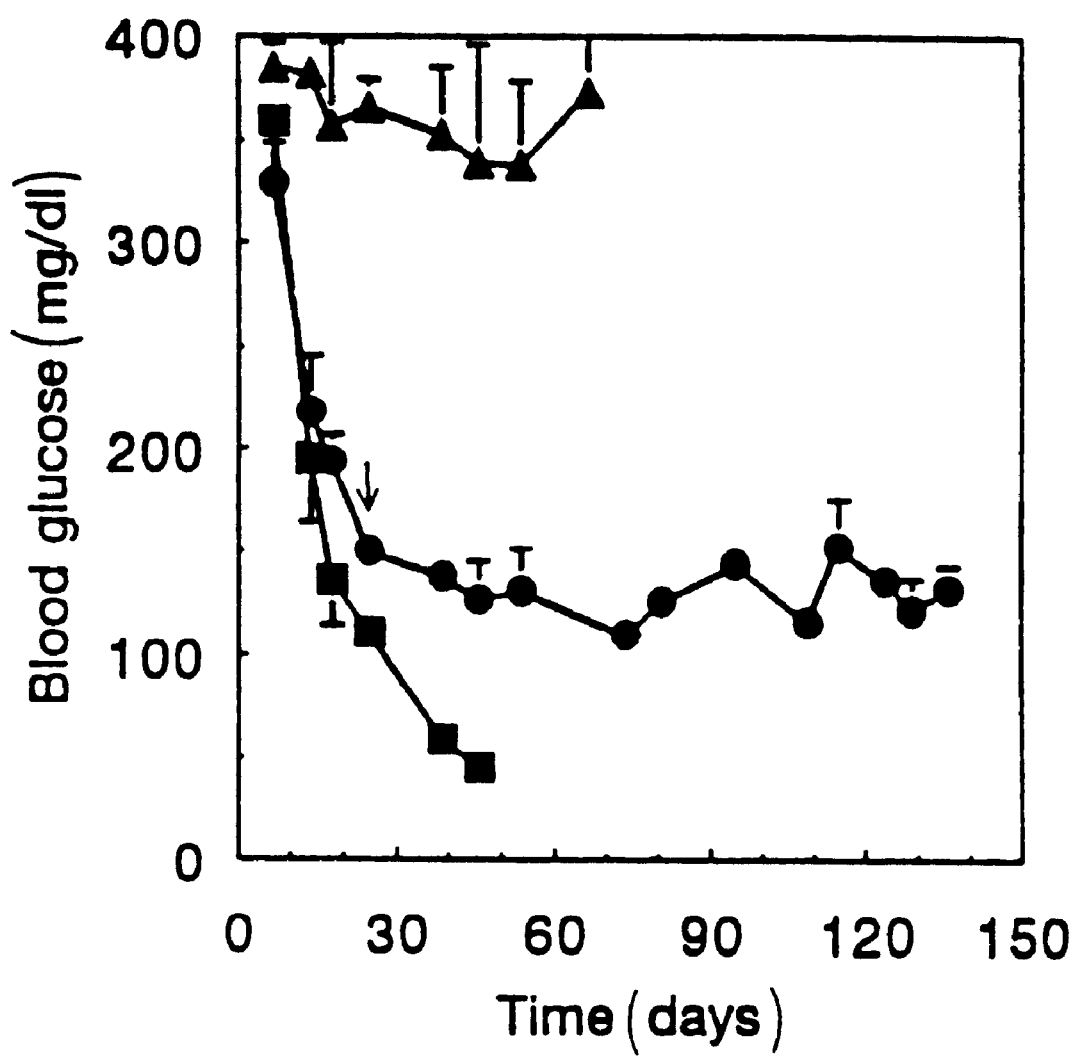
FIG. 5 shows that βTC-tet cells maintain normal blood glucose levels in diabetic recipients. Mice made diabetic by treatment with streptozotocin were implanted intraperitoneally with $2 \times 10^6$ cells (circles, squares) or received no cell implant (triangles). The time of cell implantation is shown as day 0. Blood glucose levels were measured weekly. When blood glucose was corrected, mice in one group (circles) were implanted with slow-release Tc pellets (arrow). Blood glucose levels in this group remained stable, while in the group that was not treated with Tc (squares) blood glucose continued to decrease as a result of uncontrolled proliferation of the insulin-secreting cells. Hypoglycemia in this group resulted in death of one tumor-bearing mouse at 32 days and two mice at 50 days. Values are mean±SEM (n=4). The difference between the two groups injected with cells±Tc at the 39 and 46 days time points is significant by t test ($p<0.01$).

The βTC-tet cells demonstrate correct responsiveness to glucose in the physiological concentration range (data not shown). To evaluate their capacity to maintain glucose homeostasis in vivo, βTC-tet cells were implanted into diabetic recipients (FIG. 5). The cell implantation led to correction of hyperglycemia within two weeks, demonstrating the ability of βTC-tet cells to function as normal β cells in vivo. As observed in the past with other βTC lines, the implanted cells continued to proliferate in mice not treated with Tc, which resulted in hypoglycemia and premature death. In contrast, in mice implanted with slow-release Tc pellets blood glucose levels were stabilized in the normal range. The normal blood glucose levels were maintained for as long as the mice were followed, 4 months after Tc implantation. These results indicate that the cells undergo growth arrest as a result of Tc-induced inhibition of Tag expression, but remain viable and capable of normal glucose sensing and insulin production and secretion.

C. Discussion

These results demonstrate the ability to regulate oncogene expression and cell proliferation by controlling the binding of the tetR to its cognate operator sequence in the presence of Tc or its derivative ATc. The concentration of Tc required for complete inhibition of cell replication is less than 0.1 μg/ml. ATc, which binds to tetR with a higher affinity, can achieve this effect at a 100-fold lower concentration. At the same time, ATc has a very weak antibiotic activity, since its binding to the ribosome is greatly reduced, compared with Tc (18). These properties render ATc a more attractive ligand for prolonged treatments in vivo.

A 7-day incubation of βTC-tet cells in the presence of 1 μg/ml Tc did not eliminate completely the Tag protein from all the cells, as judged by immunohistochemical analysis. In contrast, following a 7-day Tc treatment in vivo, no Tag was detected. This may represent prolonged stability of Tag protein or mRNA in culture, or leakiness of the regulator system. However, it should be pointed out that the transforming activity of Tag requires threshold levels of the oncoprotein (19) that are sufficient for stoichiometric interactions, such as titration of tumor suppressor gene products. As demonstrated by the BrdU and [$^3$H]thymidine incorporation assays, the Tc treatment likely downregulated Tag levels below this functional threshold.

These results reveal the dependence of the transformed β cells on continuous expression of the Tag oncoprotein for their proliferation. The development of β-cell tumors in these mice is a rare event, occurring in 1–2% of the islets. This has suggested the involvement of additional genetic changes in the cells. However, our results indicate that these changes most likely do not include mutations in genes that regulate the cell cycle, since the cells continue to require the activities of Tag to remain in cycle.

The ability to control cell proliferation in vivo by administration of Tc in the drinking water or with slow-release pellets, and the fact that inhibition of gene expression by Tc is reversible upon drug removal, provide an experimental system for studying the role of the Tag oncoprotein at various stages of tumorigenesis. In addition, the tet-Tag mice will allow the derivation of conditionally-transformed cell lines from other cell types, by targeting the expression of the tTA fusion protein with the appropriate cell-specific promoters. Similarly, the mice expressing the tTA protein in β cells can be used to obtain reversible expression of other genes of interest in these cells by crossing them with mice expressing such genes under control of the Tc operator minimal promoter.

The βTC-tet cell line will allow studies on the effect of cell proliferation on the expression of differentiated functions in β cells. The results obtained with cells transplanted into diabetic mice demonstrate that insulin secretion from the growth-arrested βTC-tet cells remains correctly-regulated, which enables them to maintain blood glucose levels in the physiological range. To determine the effect of cell proliferation on glucose-induced insulin synthesis and secretion in these cells, cells propagated in culture and induced to undergo growth-arrest in the presence of Tc will be studied in comparison with actively proliferating cells cultured in the absence of Tc. The strategy described here will contribute to the development of β-cell lines for cell therapy of diabetes, as well as to generation of conditionally-transformed cell lines from other cell types with therapeutic potential.

References

1. D'Ambra, R., et al. *Endocrinology* 126:2815–2822 (1990).
2. Efrat, S., et al. *Proc. Natl. Acad. Sci. USA* 85:9037–9041 (1988).
3. Miyazaki, J.-I., et al. *Endocrinology* 127:126–132 (1990).
4. Radvanyi, F., et al. *Mol. Cell. Biol.* 13:4223–4232 (1993).
5. Hamaguchi, K., et al. *Diabetes* 40:842–849 (1991).
6. Efrat, S., et al. *Diabetes* 42:901–907 (1993).
7. Ishihara, H., et al. *Diabetologia* 36:1139–1145 (1993).
8. Sakurada, M., et al. *Endocrinology* 132:2659–2665 (1993).
9. Tal, M., et al. *Mol. Cell. Biol.* 12:422–432 (1992).
10. Asfari, M., et al. *Endocrinology* 130:167–178 (1992).
11. Gazdar, A. F., et al. *Proc. Natl. Acad. Sci. USA* 77:3519–3523 (1980).
12. Nielsen, D. A., et al. *J. Biol. Chem.* 260:13585–13589 (1985).
13. Gossen, M. and Bujard, H. *Proc. Natl. Acad. Sci. USA* 89:5547–5551 (1992).
14. Hanahan, D. *Nature* 315:115–122 (1985).
15. Huang, M. T. F. and Gorman, C. M. *Nuc. Acids Res.* 18:937–947 (1990).
16. Hogan, B., et al. (1986) *Manipulating the Mouse Embryo* (Cold Spring Harbor Laboratory Press, Plainview, N.Y.).
17. Efrat, S. and Hanahan, D. *Mol. Cell. Biol.* 7:192–198 (1987).
18. Degenkold, J., et al. *Antimicrob. Agents Chemother.* 35:1591–1595 (1991).
19. Efrat, S. and Hanahan, D. (1989) in *Transforming Proteins of DNA Tumor Viruses* (Knippers, R. and Levine, A. J., eds), pp. 89–95, Springer-Verlag, Berlin.

All publications mentioned hereinabove are hereby incorporated in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for producing a recombinant, glucose-regulated insulin-producing beta cell whose proliferation is controlled by tetracycline or a derivative thereof, comprising the steps of:

(a) introducing into the genome of a first mouse a first nucleic acid comprising a DNA molecule encoding a tetracycline responsive transcriptional activator operatively linked to an insulin promoter, wherein said tetracycline responsive transcriptional activator is expressed in the beta cells of said first mouse, thereby generating a first genetically modified mouse;

(b) introducing into the genome of a second mouse a second nucleic acid comprising a DNA molecule encoding SV40 T antigen operatively linked to a tetracycline operator minimal promoter, thereby generating a second genetically modified mouse;

(c) crossing said first genetically modified mouse or offspring thereof with said second genetically modified mouse or offspring thereof, to obtain progeny of said first and second genetically modified mice;

(d) screening said progeny for doubly transgenic mice that bear a beta cell tumor wherein said tetracycline responsive transcriptional activator acts upon the tetracycline operator minimal promoter such that beta cell proliferation is controlled by tetracycline or a derivative thereof; and (e) isolating a recombinant, glucose-regulated insulin-producing beta cell whose proliferation is controlled by tetracycline or a derivative thereof, and wherein said beta cell is glucose regulated in the range of 5–15 mM.

2. An isolated recombinant, insulin-producing beta cell, said cell being glucose-regulated in the range of 5–15 mM, said cell containing a nucleic acid sequence comprising a DNA encoding a tetracycline responsive transcriptional activator operably linked to an insulin promoter, said DNA being expressed in said cell, and said cell further containing a nucleic acid sequence comprising a tetracycline operator minimal promoter operably linked to a DNA encoding SV40 T antigen, wherein the transcriptional activator acts upon the tetracycline operator minimal promoter such that cell proliferation is controlled by tetracycline or a derivative thereof.

3. The beta cell of claim 2 deposited wit h the ATCC under Accession Number CRL-11869.

4. A method for producing a recombinant insulin-producing beta cell, said cell being glucose-regulated in the range of 5–15 mM and whose proliferation is controlled by tetracycline or a derivative thereof, comprising the steps of:

(a) introducing into a beta cell in vitro
   (i) a first nucleic acid comprising a DNA molecule encoding a tetracycline responsive transcriptional activator operatively linked to an insulin promoter; and
   (ii) a second nucleic acid comprising a DNA molecule encoding SV40 T antigen operatively linked to a tetracycline operator minimal promoter;

wherein said first and second nucleic acids are stably integrated into said beta cell; and (b) screening for an isolated recombinant, glucose-regulated insulin-producing beta cell whose proliferation is controlled by tetracycline or a derivative thereof, and wherein said beta cell is glucose-regulated in the range of 5–15 mM.

5. A recombinant beta cell produced by the method of claim 4.

* * * * *